United States Patent [19]

Daniel

[11] 4,390,728

[45] Jun. 28, 1983

[54] PROCESS FOR CONVERSION OF TOLUENE TO BENZALDEHYDE

[75] Inventor: Chelliah Daniel, Columbus, Ohio

[73] Assignee: Ashland Oil, Inc., Ashland, Ky.

[21] Appl. No.: 328,290

[22] Filed: Dec. 7, 1981

[51] Int. Cl.$^3$ .............................................. C07C 45/33
[52] U.S. Cl. .................................... 568/431; 252/437
[58] Field of Search ......................................... 568/431

[56] References Cited

U.S. PATENT DOCUMENTS

| | | | |
|---|---|---|---|
| 1,636,854 | 7/1927 | Craver | 568/431 |
| 2,648,638 | 8/1953 | Richter | 568/431 X |
| 3,236,782 | 2/1966 | Koch | 568/431 X |
| 3,423,466 | 1/1969 | Guyer, Jr. et al. | 568/431 |
| 3,485,876 | 12/1969 | van de Mond | 568/431 X |
| 3,579,589 | 5/1971 | Delmon | 568/431 |
| 4,243,612 | 1/1981 | Throckmorton et al. | 568/431 |

FOREIGN PATENT DOCUMENTS 7209921 1/1973 Netherlands ........................ 568/431

*Primary Examiner*—Bernard Helfin
*Attorney, Agent, or Firm*—John F. Jones

[57] ABSTRACT

Benzaldehyde is prepared by the oxidation of toluene in the presence of a catalyst composed of the oxides of copper, iron, uranium, lead, tellurium, molybdenum, and phosphorous which can also include some other promoter elements.

4 Claims, No Drawings

PROCESS FOR CONVERSION OF TOLUENE TO BENZALDEHYDE

This invention relates to a process for the manufacture of benzaldehyde from toluene by the partial oxidation of toluene with molecular oxygen at an elevated temperature in the presence of a catalyst which conforms to the empirical formula $Cu_aFe_bU_cPb_dP_eTe_fMo_gO_x$ wherein a is 0.5–6.0, b is 0.5–2.0, c is 0.5–6.0, d is 0.5–1.0, e is 0.01–2.0, f is 0.01–2.0, g is 6.0–12.0 and x represents the number of oxygens required to satisfy the uncombined positive valences of the other elements shown in the formula.

Benzaldehyde (or benzoic aldehyde) has been manufactured from toluene in the past. One method of the prior art involves causing chlorine to react with toluene followed by hydrolysis of the dichlorinated product. This process results in the formation of numerous by-products and the cost is high because of the cost of chlorine. The direct oxidation of toluene to benzaldehyde has been proposed and this approach appears attractive because it offers the advantage of using as gaseous reactant, instead of chlorine, a very cheap and readily available gas such as air, oxygen, or an oxygen-containing mixture with inert gas or gases. Such oxidation requires the use of a solid catalyst. There is still some difficulty in carrying out selectivity of the catalytic oxidation of toluene to benzaldehyde under advantageous conditions because of the concurrent formation of substantial amounts of undesired by-products and the destructive oxidation of a part of the toluene reactant. The catalytic oxidation of toluene to benzaldehyde in the presence of a solid catalyst composed of the oxides of molybdenum and uranium at a temperature preferably about 600° C. is described in U.S. Pat. No. 3,579,589. The present invention represents an improvement in the prior art in that lower oxidation reaction temperatures can be used with the catalyst of this invention to give improved yields of benzaldehyde from toluene.

It is usual to define as per pass conversion the proportion of the reactant, toluene in this case, which is converted in each single pass over the catalyst either to the desired product, benzaldehyde, or to benzaldehyde and all other products. The per pass yield means the proportion of the reactant converted in each pass over the catalyst (once through the reactor) to the desired product. By selectivity is meant the ratio of the amount of reactant converted to the desired product to the total amount of converted reactant. Thus, the selectivity is responsible for the total yield of the process, taking into account the recycling of the unconverted reactant. In the case of the oxidation of toluene to benzoic aldehyde there could not be expected, up to now, more than a low conversion rate per pass if the selectivity was to be maintained at an acceptable level, which level was nevertheless, relatively low.

In accordance with the process of the present invention per pass conversions of toluene are usually in the range of from 35% to 50%, selectivities to benzaldehyde are in the range of from 40% to 70%, and per pass yields of benzaldehyde from toluene are in the range of from 20% to 25%.

The method of preparation of the catalysts useful in the process of this invention is not critical. Generally, it is convenient to prepare the catalyst by forming a slurry of the various ingredients which can be salts of the required elements. The slurry is preferably an aqueous slurry and the salts or compounds of the required elements can be either water soluble or insoluble. The water is usually removed from the slurry by evaporation and the resulting solid is calcined in the presence of oxygen which may be in the form of air.

The catalysts useful in this invention can also include in them support or carrier materials which include alumina, silica, magnesia, zirconia, quartz, diatomaceous earth, carbon, or silicon carbide. The support, when present, can be incorporated into the catalyst before, during, or after the slurry step.

The calcination step should be carried out at a temperature between about 400° C. and 1000° C. and preferably from 400° to 800° C.

The oxidation of toluene is carried out at a temperature of from 450° C. to 575° C. and preferably from 475° C. to 550° C. at a pressure of from atmospheric or near atmospheric up to about 10 atmospheres or higher. Preferably the oxidation process of this invention is carried out at about atmospheric pressure and at a temperature of from 500° to 525° C.

The gas accompanying the oxygen in the feed can be any gas which is inert in the reaction such as nitrogen, carbon dioxide, or steam. The proportion of inert gas to oxygen is not critical; they are selected usually in such a proportion so as to avoid forming an explosive mixture with toluene vapor. Air is a very convenient form of oxygen and inert gas.

The respective proportions of toluene and oxygen are important for the successful conduct of the process of this invention. The ratio by volume of toluene vapor to oxygen should be between about 0.1 to 2 and is preferably about 0.5.

The following examples are provided to further illustrate the present invention.

EXAMPLE I

A three step slurry procedure was used to prepare a catalyst for the process of this invention. In the first step a slurry was made using 106.0 grams of ammonium molybdate, 6.6 grams of diammonium phosphate, 68.2 grams of cupric chloride, 6.6 grams of lead nitrate and 400 ml. of deionized water. The slurry was dried at 120° C. with constant stirring for 8 hours and the resulting solid was calcined at 450° C. for 15 hours. In the second step the powdered material from the first step was mixed with 14.210 grams of tellurium dioxide, 152.2892 grams of uranyl nitrate, 81.502 grams of ferric nitrate and 20 cc. of concentrated hydrochloric acid. This slurry was also dried and calcined at 450° C. for 15 hours. In the last step the powdered product of the second step was mixed with 200 ml. of Ludox 40-HS aqueous silica sol (DuPont) containing 40% by Wt. $SiO_2$, and the dried product was calcined at 450° C. for 15 hours and then at 610° C. for 2 hours. The final catalyst composition was found by analysis to have the empirical formula $Cu_{4.0}Fe_{2.0}U_{3.0}Pb_{0.2}P_{0.5}Te_{0.9}Mo_{6.0}O_x/SiO_2$ 25%.

EXAMPLE II

The conversion of toluene to benzaldehyde by passing a feed mixture composed of toluene, oxygen, nitrogen and water in the mole ratio 7.6:12.1:75.3:5.0, respectively over the catalyst of Example I at 505° C. was carried out as follows: 15 cc. of the catalyst was used in a fixed bed reactor. Using a contact time of 1.2 seconds the reaction resulted in a 37.79% per pass conversion of toluene and a selectivity to benzaldehyde of 63.7%

(24.1% per pass yield of toluene to benzaldehyde). Using a contact time of 1.25 seconds at 480° C., the single pass conversion of toluene was 34.1% with benzaldehyde selectivity of 63.5%.

EXAMPLE III

A three step procedure using a slurry method similar to that of Example I was repeated to give a catalyst of another composition. In the first step a slurry was made from 95.0 g. of diammonium phosphate, 50.1 g. of cupric chloride, 24.0 g. of lead nitrate and 400 ml. of deionized water. The slurry was dried at 120° C. with constant stirring for 8 hours and the resulting solid was calcined at 450° C. for 15 hours. In the second step the powdered material from the first step was mixed with 12.62 g. of tellurium dioxide, 126.6 g. of uranyl nitrate, 123.55 g. of ferric nitrate, and 20 cc. of concentrated hydrochloric acid. This slurry was also dried and calcined at 450° C. for 15 hours. In the last step the powdered product of the preceding step was mixed with 240.0 ml of Ludox 40-HS (DuPont) aqueous silica sol containing 40% wt. solids and the slurry was dried at 120° C. The final product was calcined at 450° C. for 15 hours and then at 610° C. for 2 hours. The final catalyst composition was found by analysis to have the empirical formula $Cu_{3.0}Fe_{3.0}U_{2.5}Pb_{0.8}P_{0.5}Te_{0.8}MO_{5.0}O_x/SiO_2$ 30%.

EXAMPLE IV

The procedure described in Example II was repeated using the catalyst of Example III and a feed of toluene:oxygen:nitrogen:water in the mole ratio of 7.6:12.1:75.3:5.0 respectively. The conversion of toluene in a single pass was 30% and the single pass selectivity of benzaldehyde was 55.62%.

EXAMPLE V

A repeat of the procedure of Example IV except that the contact time was 1.25 seconds, the reaction temperature was 500° C., and the molar ratio of toluene:oxygen:nitrogen:water in the feed was 5.0:12.1:78.0:5.0, respectively gave a 29.3% single pass conversion of toluene with a selectivity of 51.8% to benzaldehyde.

I claim:

1. A process for the catalytic oxidation of toluene to benzaldehyde comprising contacting a catalyst with a gaseous feed stream containing toluene and oxygen at a temperature in the range of from 475° C. to 550° C. wherein the catalyst is one conforming to the empirical formula $Cu_aFe_bU_cPb_dP_eTe_fMo_gO_x$ wherein a is 0.5–6.0, b is 0.5–2.0, c is 0.5–6.0, d is 0.05–1.0, e is 0.01–2.0, f is 0.1–2.0, g is 6–12, and x represents a number determined by satisfying the sum of the unshared positive valences of the other elements shown in the formula.

2. The process of claim 1 wherein the temperature is in the range of from 500° C. to 525° C.

3. The process of claim 3 wherein the catalyst has the empirical formula: $Cu_{4.0}Fe_{2.0}U_{3.0}Pb_{0.2}P_{0.5}Te_{0.9}MO_{6.0}O_x/SiO_2$ 25%.

4. The process of claim 3 wherein the catalyst has the empirical formula: $Cu_{3.0}Fe_{3.0}U_{2.5}Pb_{0.8}P_{0.5}Te_{0.8}MO_{5.0}O_x/SiO_2$ 30%.

* * * * *